(12) United States Patent
Ye

(10) Patent No.: US 9,173,452 B2
(45) Date of Patent: Nov. 3, 2015

(54) FOOT SHAPE MEASURER

(71) Applicant: Jianxin Ye, Ouhai (CN)

(72) Inventor: Jianxin Ye, Ouhai (CN)

( * ) Notice: Subject to any disclaimer, the term of this patent is extended or adjusted under 35 U.S.C. 154(b) by 120 days.

(21) Appl. No.: 14/152,930

(22) Filed: Jan. 10, 2014

(65) Prior Publication Data
US 2015/0131865 A1   May 14, 2015

(51) Int. Cl.
*G06K 9/00*    (2006.01)
*A43D 1/02*    (2006.01)
*G06T 7/60*    (2006.01)

(52) U.S. Cl.
CPC . *A43D 1/02* (2013.01); *G06T 7/602* (2013.01); *G06T 2207/30196* (2013.01)

(58) Field of Classification Search
None
See application file for complete search history.

(56) References Cited

U.S. PATENT DOCUMENTS

| | | | |
|---|---|---|---|
| 3,027,658 A * | 4/1962 | Rigsby | 36/97 |
| 5,371,957 A * | 12/1994 | Gaudio | 36/50.1 |
| 2006/0053658 A1* | 3/2006 | Voughlohn | 36/50.1 |
| 2008/0060167 A1* | 3/2008 | Hammerslag et al. | 24/68 SK |
| 2008/0184574 A1* | 8/2008 | Press | 33/512 |
| 2010/0263236 A1* | 10/2010 | Carboy et al. | 36/117.1 |
| 2013/0269210 A1* | 10/2013 | Woods | 36/50.1 |

* cited by examiner

*Primary Examiner* — Hadi Akhavannik
(74) *Attorney, Agent, or Firm* — White and Williams LLP

(57) ABSTRACT

An apparatus for measuring feet, for the purpose of gathering measurements for custom shoes, is disclosed. The apparatus is shaped like a shoe, and has an opening where the shoe lace opening is normally present on the shoe, in addition to openings near the big toe and the little toe. Each opening has holes for laces that are tightened so that the gap, or overlap, of the openings can be measured. Additionally, mats of known thickness can be used to measure the distance between the heel of the shoe and the heel of the foot. Furthermore, markings are used to identify the different shoe lace holes so measurements can be taken at multiple places along the top of the foot. Furthermore, a size indicator can be shown on the shoe, so that measurements can be taken on a picture of the foot in the shoe rather than on the foot and shoe themselves, and then scaled to actual size with reference to the size indicator.

14 Claims, 1 Drawing Sheet

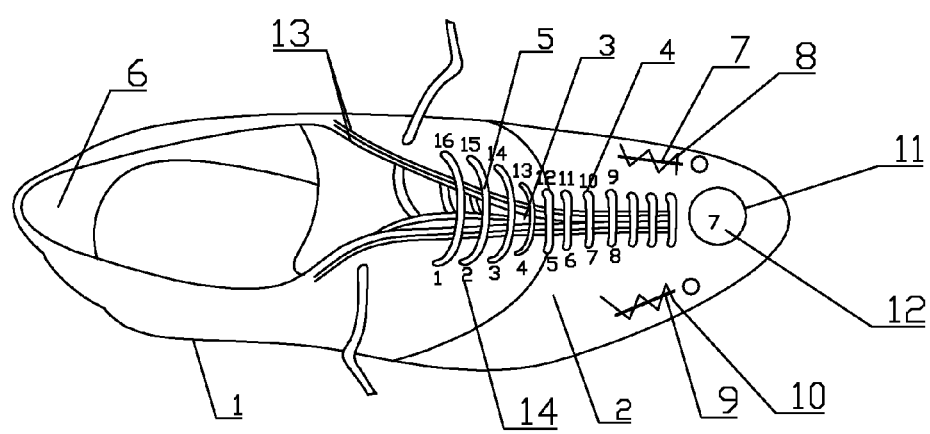

FOOT SHAPE MEASURER

CROSS-REFERENCE TO RELATED APPLICATIONS

This application claims the benefit of Chinese Patent Application No. 201320719496.9, filed Nov. 19, 2013 and Chinese Patent Application No. 201320854096.9, filed Dec. 23, 2013 both of which are incorporated herein by reference in their entirety.

FIELD OF THE INVENTION

The present invention is an apparatus for measuring the size of feet, e.g. for use in making custom shoes.

BACKGROUND

Current technology for custom shoe makers to measure the size of their customers' feet includes methods such as 3D scanner, plaster reverse mould, manual measuring and so forth. These conventional ways of measuring only collect data. Therefore, due to factors such as the differences of material, style, and manufacture crafts, a custom-made shoe can only be made after repeated attempts to measure. In addition, foot-size measuring by applying conventional methods or 3D scanning demands a high degree of skill in the operator, which considerably increases the costs of making shoes. Because of the expense involved, customized shoe making is available only as a luxury item. Moreover, 3D scanners are not portable, and thus require the customer to go to the site of the scanner to be measured. On the other hand, conventional manual measuring requires the shoe maker or other skilled professional to measure the size of their customer face to face. To solve the aforementioned problems, we provide a type of shoe-shape measurer, for which a picture is enough for a successful measurement.

SUMMARY OF THE INVENTION

This invention is a type of foot shape measurer that is able to accurately measure the size other foot, to determine the dimensions need to make customized shoes.

In accordance with one aspect of the present invention, a foot shape measurer takes the shape of a shoe, including the sole and upper surface; the upper surface covers the sole and fixes with it. The first opening is arranged along the length of the upper surface mentioned. The opening is located at the position 0-150 mm from the toe cap of the shoe. It extend backward, with its length more than 10 mm, the first ribbon or thread like device which is used to close and bind the two sides of the opening is arranged on the upper surface ! with many mats are arranged at the internal sides of the shoe counter.

In accordance with one aspect of the present invention, the second opening is arranged on the upper surface mentioned. The second opening is also arranged on the upper surface mentioned. It is opposite to the thumb of the foot. The two sides of the second opening are bund and closed by the second thread or ribbon like device set at the upper surface.

In accordance with one aspect of the present invention, the third opening is arranged on the upper surface mentioned. It is opposite to the small toe. The two sides of the third opening are bund and closed by the third thread or ribbon like device set at the upper surface.

In accordance with one aspect of the present invention, the reference level set on the upper surface is included.

In accordance with one aspect of the present invention, the marker level set on the upper surface is included, which is close to reference level.

In accordance with one aspect of the present invention, the first ribbon or thread like device mentioned directly contacts the foot.

In accordance with one aspect of the present invention, the marking lines are arranged at both sides of the first opening of the upper surface.

In accordance with one aspect of the present invention, the holes through which the first ribbon or thread like device goes are arranged on the upper surface. They are clearly numbered.

In accordance with one aspect of the present invention, many mats are arranged at the internal sides of the shoe counter.

Compared to the conventional solutions, this invention boasts of the following outstanding technical merits:

This invention, a type of foot shape measurer, is designed with a structure of first opening, when a wide foot is put into it, the foot shape measurer can be expanded at the position of the opening properly thanks to the function of the opening ← the position of the foot can also be limited by the ribbon or thread-like device, the size of the foot can be measured by measuring the distance of the 2 sides of the opening.

When a foot with narrow shape enters the measurer, the 2 sides of the opening can also overlap, the position of which can be limited by the ribbon or the thread like device. The size of the foot can be measured by measuring the overlapping of the 2 sides of the opening. As this device is of shoe-shape, which makes it corresponds to the shoe last. To be more specific, through acquiring the opening of the slit at any place, it may be broadened or narrowed directly at the corresponding position of the shoe last and provide direct evidence for the shoe making at later stages, which is also the essence of this invention as it has achieved the function that can not be met by other measuring devices.

The conventional way of measuring only collects data, therefore due to factors such as the differences of material, style, and manufacture crafts, a custom shoe can only be made after repeated measurements. As this foot shape measurer is made of the same material as the shoes ordered by the customer, as well as the same shape, style and crafts, the aforementioned repeated trials due to the measuring errors can effectively be avoided. Accordingly, the cost of customized shoe making, as well as the failure rate, can be reduced. In addition, this foot shape measurer enables the customers to better experience the process of shoe making, helping them to better understand the style of the shoes they want.

When measuring the foot size, the operation of this measurer is similar to putting shoes on, it is easy and convenient to operate; its usage is familiar to all, no specialized skill is needed.

This type of measurer is able to facilitate future E-business operation and be its important prerequisite, permitting custom shoe orders to be fulfilled online. Before starting to make the shoes, the shoe maker may send this foot shape measurer to the customer, and the customer would put his/her foot inside it and take pictures, and then send the picture to the shoe maker. The shoe maker would then have the data and parameters necessary to make custom shoes.

This type of foot shape measurer is of simple structure, with low manufacture cost. It is very easy and convenient to measure foot size with it. Also, it requires no specialized skill during the measurement, which effectively lowers the cost of customized shoe making by allowing the customer to perform the measurement, making it no longer a luxury and spread more widely.

The mat in-between the heel and the internal side of the shoe counter help to measure the distance between the heel and the shoe counter.

BRIEF DESCRIPTION OF THE FIGURE

FIG. 1 is a top view of the structure of one aspect of the invention.

DETAILED DESCRIPTION

Before aspects of the invention are explained in detail, it is to be understood that the invention is not limited in its application to the details of the examples set forth in the following descriptions or illustrated drawings. The invention is capable of other embodiments and of being practiced or carried out for a variety of applications and in various ways. Also, it is to be understood that the phraseology and terminology used herein is for the purpose of description and should not be regarded as limiting.

Turning now to FIG. 1, this new type foot shape measurer; takes the shape of a shoe, including sole 1 and upper surface 2. The upper surface 2 covers the sole 1 and is fixed to it. The first opening 3 is arranged on the upper surface 2, which in one aspect starts at the place 0-150 mm from the shoe toe. Its length is more than 10 mm, going along the length of the measurer, going backward from the toe or the location substantially close to the toe. The first opening 3 is positions in substantially the same manner as an ordinary opening for shoe laces would be positioned.

The first ribbon or thread like device 5 is used to close and bind the 2 sides of the first opening 3 in a manner similar to the manner in which ordinary shoes are fastened by shoe laces. When a wide foot is put into it, the foot shape measurer can be expanded at the position of the opening properly thanks to the function of the opening  the position of the foot can also be limited by the ribbon or thread like device 5, the size of the foot can be measured by measuring the distance between the 2 sides of the opening. When a foot with narrow shape enters the measurer, the 2 sides of the opening can also overlap, the position of which can be limited by the ribbon or the thread like device. The size of the foot can be measured by measuring the overlapping of the 2 sides of the opening. The mats (not shown) are placed at the internal side of the shoe counter 6. There are many mats, such mats can be used singly or overlapped. The thickness of the mats can be the same or different. The mats are placed between the heel and the shoe counter and the thickness of the mats used, corresponding to the distance between the shoe counter 6 and the heel, is measured.

As shown in FIG. 1, the shoe holes 4 are arranged at both sides of the opening 3 on the upper surface 2. The first ribbon or thread like device 5 is fixed at the shoe holes 4, the 2 sides of the opening are fastened by drawing the ribbon or thread like device 5. The ribbon or thread like device 5 may be with or without elasticity. It enables the measurer to contact tightly with the heel, so as to accurately measure the foot shape. The ribbon like device 5 can also be elastic belt, with one end directly stilted to the one side of the first opening, so as to omit the step of tying the shoe lace. The ribbon or thread like device can also be sticky belt, with one end fixed to one side of the first opening. In this aspect the shoe holes 4 are arranged on the upper surface of the measurer, through which the sticky belt goes, such holes locate at the other side of the opening mentioned. When fastening, the one end of the sticky belt goes through the shoe holes and sticks to the other end of the sticky belt after winding around the shoe measurer.

Foot shapes vary according to specific individuals, with the positions of big toe and small ("pinky") toe in particular. In order to accurately measure the size of the positions of these two toes, a second opening 7 is shown. The second opening 7 is located opposite to the thumb toe; its two sides are fastened and closed by a second ribbon or thread like device 8. A third opening 9 is also arranged on the upper surface mentioned, located opposite the small toe. It is fastened and closed by a third ribbon or thread like device 10 arranged on the upper surface 2. The manner in which measurements are taken with the second and third openings is the same as the practice of the first opening.

In this aspect, the reference level 11 on the upper surface 2 is also included. The reference can be a circle with radius of approximately 3 mm. It may also take other shapes. The foot measurer with reference level may be sent to the customer for measurement. The customer may wear the measurer and take pictures and send the pictures back to the shoe maker. By comparing the size of the reference level and the size of it in the picture, the shoe maker is then able to calculate the scale of the photo, and therefore the openness of the first opening, which provides him with adequate information on the size of widening or narrowing the size of the shoes to be made.

In this aspect, a marker level 12 is also included, which is in close proximity to reference level 11. It stands for the size of this measurer. For example, if the measurer simulates a size 10 shoe, the number of the marker level is shows the number 10.

In this aspect, marking lines 13 are set at both sides of the first opening. The marking line 13 can be engraved on upper surface 2, it may also be painted on the upper surface 2 with pigment, ink and other color materials. The marking line serves the shoe maker in measuring the overlapping amount of the upper surface in the narrow foot case.

In this aspect, the shoe holes 4 are arranged on the upper surface 2, through which the first ribbon or thread like device 5 goes. The holes are numbered 14, the position of shoe holes correspond with the shoe last. By consulting the number 14, a shoe maker is able to easily locate the position of every shoe hole in the shoe last, which facilitate them to widen or narrow or maintain the same size during the process of shoe making.

The examples noted here are for illustrative purposes only and may be extended to other implementation embodiments. While several embodiments are described, there is no intent to limit the disclosure to the embodiment(s) disclosed herein. On the contrary, the intent is to cover all alternatives, modifications, and equivalents obvious to those familiar with the art.

What is claimed is:

1. A shoe-shaped apparatus for measuring a foot inserted into the apparatus, said apparatus comprising an upper surface having: a first opening beginning on a toe end of the apparatus and extending toward a heel end of the apparatus, substantially in the horizontal center of the apparatus, said first opening having one or more first opening holes along sides of the first opening for insertion of a first lace, ribbon or thread, said first lace, ribbon or thread, when threaded through the one or more first opening holes, capable of closing the first opening; a marking line along at least one side of the first opening; identifying markings proximal to, and functional to uniquely identify, each of the first opening holes; and a second opening situated in the approximate location of a big toe of the foot, said second opening having one or more second opening holes along sides of the second opening for insertion of a second lace, ribbon or thread, said second lace, ribbon or thread, when threaded through the one or more second opening holes, capable of closing the second opening wherein said upper surface further comprises a third opening situated in the approximate location of a small toe of the foot, said third opening having one or more third opening holes along sides of the third opening for insertion of a third lace, ribbon or thread, said third lace, ribbon or thread, when threaded through the one or more third opening holes, capable of closing the third opening.

2. The apparatus of claim 1, further comprising at least one mat designed to be placed between a heel of the foot and an interior back of the apparatus.

3. The apparatus of claim 1, wherein said upper surface comprises a marking line along two sides of the first opening.

4. The apparatus of claim 3, wherein the sides of the opening are able to overlap one another when the foot is sufficiently narrow to permit overlap.

5. The apparatus of claim 1 further comprising a size marker.

6. The apparatus of claim 1 wherein one end of the first lace, ribbon, or thread is attached to one side of the first opening.

7. A method of measuring the dimensions of a foot, comprising the steps of inserting the foot into a shoe-shaped apparatus; tightening a first lace, ribbon or thread that has been threaded into to a set of first opening holes along two sides of a first opening in an upper surface of the apparatus, until the apparatus fits comfortably around the foot; tightening a second lace, ribbon or thread that has been threaded into a set of second opening holes along two sides of a second opening located in the approximate location of a big toe of the foot; measuring a distance between a first side of the first opening and a second side of the first opening; and measuring a distance between a first side of the second opening and a second side of the second opening, tightening a third lace, ribbon or thread that has been threaded into a set of third opening holes along two sides of a third opening located in the approximate location of a small toe of the foot; and measuring a distance between a first side of the third opening and a second side of the third opening.

8. The method of claim 7, further comprising the steps of:
inserting at least one mat between a heel of the foot and the interior back of the apparatus; and
measuring the thickness of the at least one mat.

9. The method of claim 7, wherein said measuring a distance between a first side of the first opening and a second side of the first opening comprises measuring the distance between a first marking line on the first side of the first opening and a second marking line on the second side of the first opening.

10. The method of claim 9, wherein the first side of the first opening overlaps the second side of the first opening.

11. The method of claim 7, further comprising the step of taking a photograph of the foot in the apparatus, wherein the steps of measuring the distance between the first side of the first opening and the second side of the first opening; and measuring the distance between the first side of the second opening and the second side of the second opening, are performed on the photograph.

12. The method of claim 11, further comprising referring to a size marker on the shoe to determine the scale of the photograph.

13. The method of claim 7, further comprising the step of measuring the distance between the first side of the first opening and the second side of the second opening at a plurality of locations along the first opening.

14. The method of claim 13, further comprising the step of referring to identifying markings proximal to, and functional to uniquely identify, each of the first opening holes.

* * * * *